United States Patent [19]
Bradshaw et al.

[11] 3,998,101
[45] Dec. 21, 1976

[54] METHOD AND APPARATUS FOR SAMPLING THE ATMOSPHERE IN NON-HERMETICALLY-SEALED CONTAINERS

[75] Inventors: Robert Fagan Donat Bradshaw, Markyate; Colin Frank Richardson Wainwright, Chesham, both of England

[73] Assignee: U.S. Philips Corporation, New York, N.Y.

[22] Filed: July 31, 1975

[21] Appl. No.: 600,607

[30] Foreign Application Priority Data

Apr. 30, 1975 United Kingdom ............. 37795/75

[52] U.S. Cl. .................................... 73/421.5 R
[51] Int. Cl.² ................................... G01N 1/22
[58] Field of Search ............. 73/421.5 R, 23.1, 19, 73/23; 250/358, 359, 360

[56] References Cited
UNITED STATES PATENTS 3,568,411 3/1971 Dravnieks ..................... 73/23.1
3,617,734 11/1971 Chaudet et al. ................ 73/23

Primary Examiner—Donald O. Woodiel
Attorney, Agent, or Firm—Frank R. Trifari; Leon Nigohosian

[57] ABSTRACT

A method and apparatus for detecting the presence of vapor-producing substances such as explosives contained within an item of baggage, in which the item of baggage is enclosed in a chamber and the air pressure in the chamber is varied cyclically in order to mix at least a portion of the air in the item of baggage with that in the chamber. A vapor detector is then used to detect the presence in the chamber air of vapors given off by an explosive substance or drug (e.g., cannabis) contained within the item of baggage.

31 Claims, 3 Drawing Figures

METHOD AND APPARATUS FOR SAMPLING THE ATMOSPHERE IN NON-HERMETICALLY-SEALED CONTAINERS

This invention relates to a method and apparatus for sampling the atmosphere in a non-hermetically-sealed container and more particularly to a method and apparatus for detecting the presence of volatile organic substances, such as explosives or certain drugs, in a non-hermetically-sealed container. It has particular but not exclusive application to the inspection of traveller's hand baggage at airways terminals and similar locations.

Explosives detectors are known which operate by detecting the presence of the vapors given off by certain explosives. Heretofore it has been necessary to open each item of baggage, at least sufficiently to insert the probe of an explosives detector, in order to determine whether or not explosives are contained therein. This procedure is time-consuming and objectionable to the travellers concerned. It is therefore desirable to obtain a sample of the atmosphere within a non-hermetically-sealed container such as an item of baggage without either opening or physically penetrating the baggage.

It has been proposed to place items of baggage singly inside a substantially hermetically-sealed chamber, in which the air pressure is then either raised or lowered. On the return of the pressure to normal, some of the atmosphere within the item of baggage will have mixed with the air in the chamber due to interchange of air through natural leaks in the baggage during the changes of pressure. The air in the chamber is then tested for the presence of explosives vaporss. In order to accommodate the varying shapes and sizes of items of hand baggage, the chamber must be of substantial volume. Moreover, a considerable change of pressure is necessary in order to achieve a sufficient transfer of atmosphere from within the baggage. Hence the chamber must be strongly built and adequate pumping capacity must be provided. The procedure is also liable to be time consuming.

It is an object of the present invention to provide a rapid and simple method for mixing the atmosphere in a non-hermetically-sealed container with that in a surrounding chamber.

According to a first aspect of the invention there is provided a method for sampling the atmosphere in a non-hermetically-sealed container, the method comprising the steps of locating the container within a substantially closed chamber, cyclically varying the pressure within the chamber at a given repetition rate and within a given pressure range, and then sampling the atmosphere within the chamber.

According to a second aspect of the invention there is provided a method for detecting the presence of a volatile organic substance contained within a non-hermetically-sealed container, the method comprising the steps of locating the container within a substantially closed chamber, cyclically varying the pressure within the chamber at a given repetition rate and within a given pressure change range, and then determining whether or not any vapor from the substance is present in the atmosphere within the chamber.

According to a third aspect of the invention there is provided apparatus for sampling the atmosphere in a non-hermetically-sealed container, the apparatus comprising a substantially-closable chamber of a size sufficient to envelop said container, means for cyclically varying the pressure within the chamber at a given repetition rate and within a given pressure range, and a sampling device so arranged as to sample the atmosphere within the chamber.

According to a fourth aspect of the invention there is provided apparatus for detecting the presence of a volatile organic substance contained within a non-hermetically-sealed container, the apparatus comprising a substantially-closable chamber of a size sufficient to envelop said container, means for cyclically varying the pressure within the container at a given repetition rate and within a given pressure range, and a detector for detecting the presence of any vapour from said substance in the chamber.

During each cycle of pressure change a small proportion of the atmosphere within the container emerges into the chamber. By allowing the pressure variation to continue for several cycles, a sufficient proportion is extracted to allow the presence of vapor-producing substances in the baggage to be detected by a vapor detector sampling the air in the chamber. If the cyclic variation of pressure were continued for a sufficient period, complete mixing of the atmosphere in the baggage and the air in the chamber could be achieved, but this is by no means necessary. It has been found that the change of pressure required in each cycle in the method and apparatus according to the invention is substantially less than that required in the known system where the pressure is raised or lowered once only. The cyclic pressure variation may be created by arranging for a part of one wall of the chamber to be flexible, and by reciprocating this flexible portion by an electric motor and crank mechanism or a solenoid, so as to cause a cyclic change of the volume of the chamber.

Optionally, the gas diffusion rate into and out of the container for a given volume change may be enhanced by providing the chamber with a vent in the form of a pipe (or horn) open to the atmosphere at its end remote from the chamber and by operating the reciprocating mechanism at a frequency such as to excite to resonance the system comprising the air in the vent and the air in the chamber. The vent pipe may be coiled or folded to fit into a conveniently-shaped space.

It will be appreciated that for the complete screening of travellers, in addition to examining baggage for the presence of explosives or drugs, it is necessary to examine both the baggage and the travellers themselves for the presence of concealed weapons. It is known to employ metal detectors to indicate the presence of metallic objects such as guns and knives concealed on the traveller's person and to subject items of baggage to X-ray examination. The present invention may be utilised in conjunction with these methods to provide an improved security system.

In order that the invention and the manner in which it is to be performed may be more clearly understood, an embodiment thereof will be described by way of example with reference to the accompanying drawings, of which:

Figure 1:
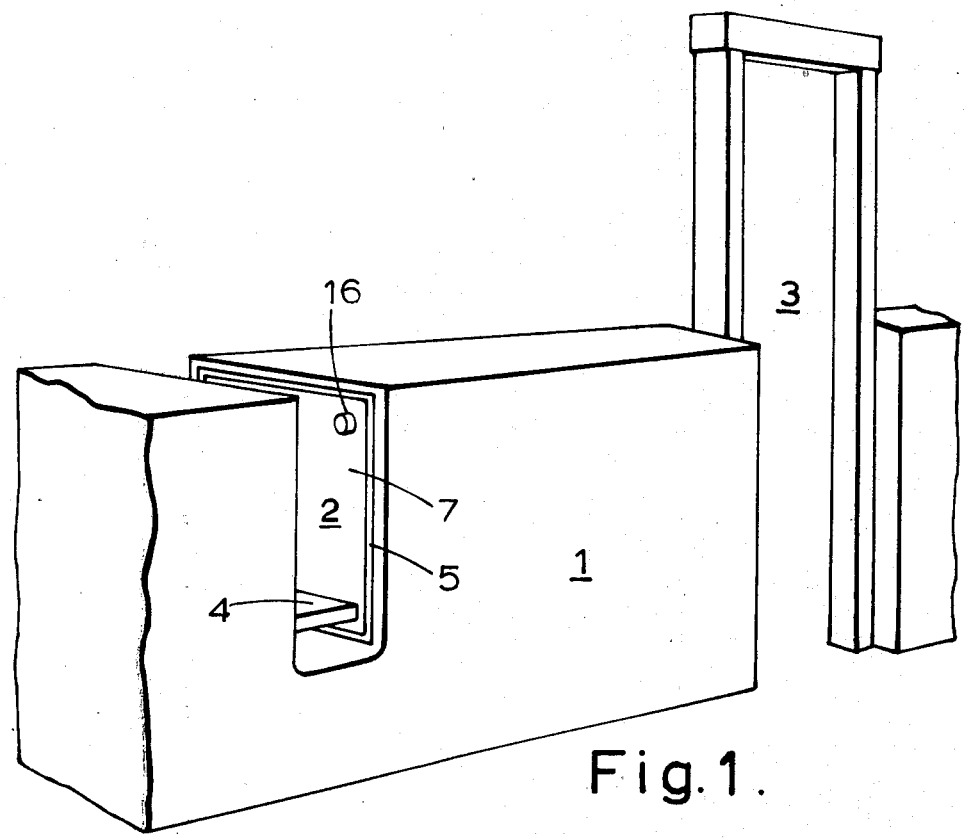
FIG. 1 is a perspective view of a security barrier embodying the invention.

Referring first to FIG. 1, a security barrier comprises fence 1 separating unscreened and screened areas and provided with a generally U-shaped transverse trough 2 for the reception and examination of hand baggage, and a gateway 3. In use, an intending traveller approaches the barrier on the "unscreened" side, places this hand baggage on a shelf 4 projecting from one wall of the trough 2, passes through the gateway 3, which may, for example, be equipped with metal detection apparatus (not shown in the drawing) which is effective to indicate the presence of weapons on his person, and recovers his baggage from the trough 2, on the "screened" side of the barrier. During the time taken for the traveller to pass from one end of the trough through the gateway to the other end of the trough, the baggage is subjected both to X-ray examination for solid objects such as guns and also to examination for explosives and/or drugs. Shelf 4 may, optionally, be a weighing platform for weighing each item of baggage.

X-ray apparatus of known type (not shown in FIG. 2) may be mounted in the walls of the trough 2 to produce a picture of the contents of the baggage on an adjacent visual display unit. To protect both security personnel and travellers from irradiation by X-rays a lead-lined screen (shown at 6 in FIG. 2) in the form of a rectangular tube open at both ends is extended through slots 5 in one wall 7 of the trough 2 so as to abut against the opposite wall. Controls are interlocked so that the X-ray apparatus can be energized only when the screen is in the extended position.

Figure 2:
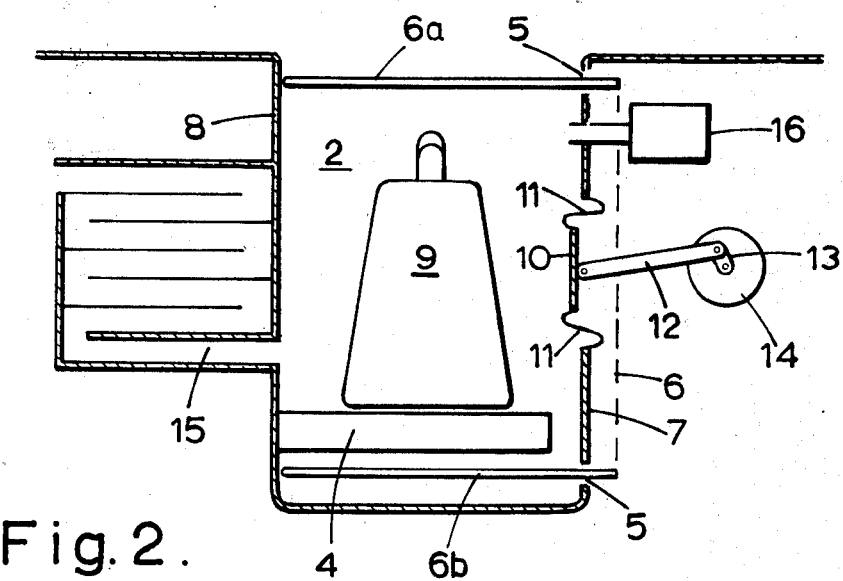
FIG. 2 is a cross-sectional view of the baggage examination chamber of the barrier in FIG. 1.

In FIG. 2 the screen 6 is shown in the extended position. The upper side 6a and the lower side 6b of the screen are shown extended through the slot 5 in the wall 7 and abutting against the opposing wall 8 of the trough 2. The vertical sides of the screen likewise abut against the wall 8. It will be appreciated that when the screen is extended, a container such as an item of baggage 9 is enclosed in a chamber comprising the screen 6 and the walls 7 and 8. Flexible (e.g. rubber) sealing strips may be provided to reduce air leakage between the screen and the walls. A plate 10 is mounted by means of a flexible diaphragm 11 in an aperture provided in the wall 7. One end of a connecting rod 12 is connected to the plate 10 and the other end is connected to a crank 13 rotatable by an electric motor 14. Typically, the crank 13 is rotated at 5 to 10 revolutions per second, reciprocating the whole plate in alternate directions transverse along a line to the wall 7 and so causing cyclic variations in the volume of the chamber and, hence, corresponding variations of the pressure therein. It is found that if the rotation of the crank is continued for a period of the order of 5 seconds, sufficient mixing of the atmospheres within the chamber and within the baggage occurs for an organic vapour detector 16 of known type (for example Pye Dynamics Ltd. Type no. L1A1), which samples the atmosphere within the chamber, to give a positive reaction if volatile organic substances, such as explosives, are contained within the baggage.

It can readily be appreciated that, with plate 10 in its central position at atmospheric pressure, reciprocation of the plate an equal distance on each side of this central position will produce substantially equal pressure changes above and below atmospheric pressure. Thus if an overall pressure change of $x$ pounds per square inch is required in the chamber, the movement of plate 10 is such as to cause a pressure change of $x/2$ in the chamber in each direction of movement. In such a system, the maximum difference between atmospheric pressure outside the chamber and the pressure within the chamber is thus only $x/2$; i.e. half that which applies in the known system previously referred to.

Optionally, there may be provided a pipe 15 (shown folded) with one end opening into the chamber and with its other end open to the atmosphere, the length of the pipe being chosen so that the system comprising the air in the chamber and the air in the pipe resonates at the frequency of reciprocation of the plate 10. The gas diffusion rate into and out of the container for a given amplitude of oscillation of plate 10 is thereby increased. The pipe 15 may alternatively be straight or may be coiled for convenience in installation. In a practical embodiment, pipe 16 was about 6 feet long and has a cross-sectional area of about 4 square inches; the oscillation frequency of the plate being 5 cycles per second. After the atmosphere has been sampled, and the X-ray examination has been completed, the screen 6 is withdrawn to permit the traveller to recover the baggage. A blast of compressed air may be utilised, either before or after the screen is withdrawn, to purge the trough of the atmosphere extracted from one piece of baggage before a further piece is inserted. Detector 16 may alternatively be located at the open end of pipe 15 remote from trough 2. In this case, the trough is purged with screen 6 in the extended position shown in FIG. 2; any vapour present in the air in trough 2 then being detected as it is being blown out via pipe 15.

In the known apparatus previously referred to, in which the pressure in the chamber is raised above or reduced below atmospheric pressure by a given amount and then allowed to return to atmospheric pressure, a pressure change in the region of 2 to 4 pounds per square inch is typically required. This not only means that the walls of the chamber have to be made very strong to withstand this pressure difference, but also means that the pumping apparatus used to produce the pressure change takes a considerable time to reach the required pressure. Also, the sealing of the chamber has to be able to withstand this pressure difference.

In the method and apparatus according to the invention, a very small pressure change is frequently repeated to achieve the same result. This gives the twofold advantage that the changes can be made very quickly, hence substantially reducing the time taken for the inspection, and that a very light construction of the chamber walls is now possible, hence substantially reducing the cost of the equipment.

In a practical test of the apparatus according to the invention, a piece of paper in which an explosive substance had previously been wrapped was placed in a brief case along with many normal documents. The brief case was then placed in the trough, and the chamber closed.

The chamber was approximately an 18 inch cube and plate 10 was a circular plate of 6 inch diameter. The plate was then reciprocated at 5 cycles per second for 5 seconds, by which time the vapour detector (Pye Dynamics Ltd. Type No. L1A1) had indicated the presence of an explosives substance within the brief case. The total deflection of the plate was one inch, giving a volume change (and hence a pressure change) within the chamber of approximately one half per cent. This is equivalent to a pressure change in the chamber of 0.07 pounds per square inch; i.e. about one-thirtieth of the minimum pressure change required in the known system.

As a very rough guide, we have found on average that effective results are achieved if the number of pressure cycles performed multiplied by the pressure change in each cycle is in the approximate order of 1 to 3 pounds per square inch. Thus at a frequency of one cycle per second and a pressure change of 0.2 pound per square inch, approximately 10 cycles are needed — i.e. an inspection time of 10 seconds. At 50 cycles per second, with a pressure change of 0.01 pounds per square inch, inspection can be completed in 4 seconds. At the lower frequencies (a few cycles per second), the time taken for the inspection is the important factor. At the higher frequencies (above 50 cycles per second) the mechanical requirements for moving the plate 10 becomes onerous. Further, as the frequency is increased, a point may be reached (dependent upon the container and upon the pressure change chosen) where mixing of the air in the container with that in the chamber becomes insufficient for effective inspection. Thus, for example, if the container concerned has a minimum air leakage path to outside the container of one inch, and if the path resistance to air flow, the pressure change per cycle, and the frequency are such that an air movement of less than 1 inch in the path is produced, then there will be substantially no leakage of vapor from the container into the chamber. We have found that a frequency range of about one to about fifty cycles per second and an approximate pressure change range of from 0.01 to 0.2 pounds per square inch gives adequate results.

Although the specific embodiments have been described with reference to the detection of explosives and/or drugs such as cannabis, the invention is equally applicable to the detection of other vapor-producing substances; an appropriate vapor detector or detectors being used for each application.

Figure 3:
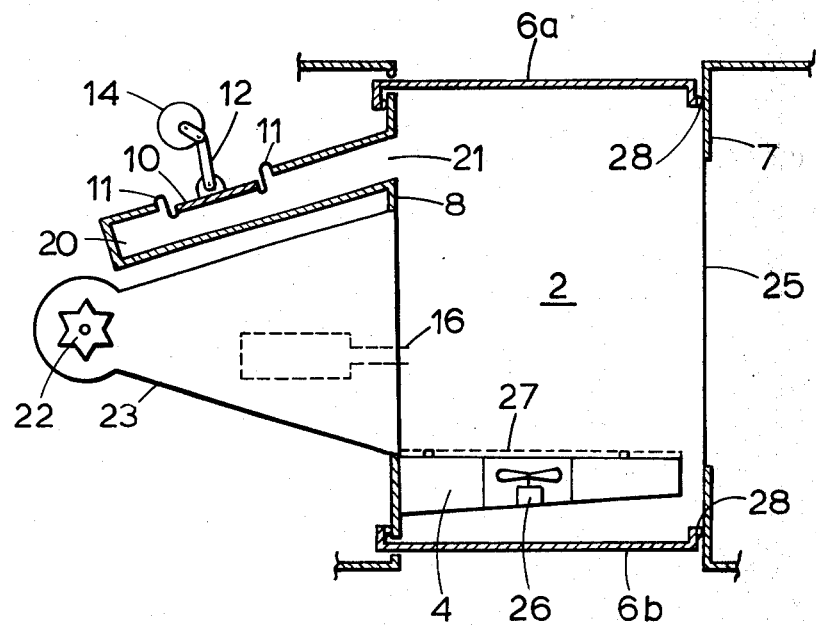
FIG. 3 shows an alternative embodiment of the baggage examination chamber.

FIG. 3 shows an alternative arrangement of apparatus according to the invention, in which Figure items corresponding to the same or similar items in FIG. 2 are given the same reference numerals. Plate 10 and flexible diaphragm 11 are now accommodated in a side chamber 20 which communicates with the main chamber 2 via an opening 21, thus largely freeing the side walls of the chamber 2 for use by X-ray apparatus. An X-ray source 22 is mounted in a screening shield 23 impervious to X-rays. The portion 24 of wall 8, which portion closes the mouth of the substantially conical screen 23, is transparent to X-rays and may comprise a rigid plastic sheet or a thin sheet of aluminium A fluorescent screen 25 is mounted in an aperture in the opposite wall 7. The fluorescent screen 25 may be viewed directly but is preferably scanned by a scanning device, such as a closed-circuit television system, so that the image on the screen 25 may be examined at a more convenient remote point. Organic vapor detector 16 may be placed in any convenient position, of course, and is shown in FIG. 3 as being mounted adjacent screen 23. A fan 26 is provided in shelf 4 to ensure an even distribution of any vapor extracted from items of baggage and also to assist in purging the chamber space 2 when the screen 6 is withdrawn. A support grid 27 is provided for baggage items. The edges of screen 6 which abut walls 7 and 8 are provided with compressible resilient sealing strips 28.

What is claimed is:

1. A method for sampling the atmosphere in a non-hermetically-sealed container, the method comprising the steps of locating the container within a substantially closed chamber, cyclically varying the pressure within the chamber at a given repetition rate and within a given pressure range, and then sampling the atmosphere within the chamber.

2. A method according to claim 1 wherein said repetition rate is in the range of about 1 to about 50 cycles per second.

3. A method according to claim 1, wherein said pressure change range is about 0.01 to about 0.2 pounds per square inch.

4. A method according to claim 3 wherein the said pressure range is atmospheric pressure ± 0.1 pounds per square inch.

5. A method according to claim 1, wherein said chamber is provided with a vent, the dimensions of the chamber and the vent being such that the air in the chamber is excited into resonance at the given repetition rate.

6. A method according to claim 1, wherein the pressure variations are produced by cyclically changing the enclosed volume of the chamber.

7. A method according to claim 6, wherein the wall of said chamber comprises a flexibly - movable portion and volume change is produced by movement of said flexibly-movable portion.

8. A method for detecting the presence of a volatile organic substance contained within a non-hermetically-sealed container, the method comprising the steps of locating the container within a substantially closed chamber, cyclically varying the pressure within the chamber at a given repetition rate and within a given pressure change range, and then determining whether or not any vapor from the substance is present in the atmosphere within the chamber.

9. A method according to claim 8, wherein said chamber is provided with a vent, the dimensions of the chamber and the vent being such that the air in the chamber is excited into resonance at the given repetition rate.

10. A method according to claim 8, wherein the pressure variations are produced by cyclically changing the enclosed volume of the chamber.

11. A method according to claim 10, wherein wall of said chamber comprises a flexibly-movable portion and the volume change is produced by movement of said flexibly-movable portion.

12. Apparatus for sampling the atmosphere in a non-hermetically-sealed container, the apparatus comprising a substantially-closable chamber of a size sufficient to envelop said container, means for cyclically varying the pressure within the chamber at a given repetition rate and within a given pressure range, and a sampling device so arranged as to sample the atmosphere within the chamber.

13. Apparatus according to claim 12, wherein the said repetition rate is in the range about 1 to about 50 cycles per second.

14. Apparatus according to claim 12, wherein the said pressure change range is about 0.01 to about 0.2 pounds per square inch.

15. Apparatus according to claim 14 wherein the said pressure range is atmospheric pressure ± 0.1 pounds per square inch.

16. Apparatus according to claim 12 including means for cyclically changing the volume of the chamber to produce said pressure variations.

17. Apparatus according to claim 16 wherein a wall of the chamber is provided with a flexibly-movable portion movement of which produces the said volume change.

18. Apparatus according to claim 17 wherein the flexibly-movable portion is movable by means of a drive mechanism.

19. Apparatus according to claim 18 wherein the drive mechanism is an electric motor.

20. Apparatus according to claim 12, including means for purging the air from the chamber.

21. Apparatus according to claim 12, wherein said chamber is provided with a vent, the dimensions of the chamber and of the vent being such that the air in the chamber and vent resonates at the given repetition rate.

22. Apparatus according to claim 21 wherein the vent has the form of a pipe one end of which opens into the chamber and the other end of which is open to the atmosphere.

23. Apparatus according to claim 12 including X-ray apparatus so arranged in relation to the chamber that the presence of metal objects within a container located in the chamber may be detected thereby.

24. Apparatus for detecting the presence of a volatile organic substance contained within a non-hermetically-sealed container, the apparatus comprising a substantially-closable chamber of a size sufficient to envelope said container, means for cyclically varying the pressure within the container at a given repetition rate and within a given pressure range, and a detector for detecting the presence of any vapor from said substance in the chamber.

25. Apparatus according to claim 24, including means for cyclically changing the volume of the chamber to produce said pressure variations.

26. Apparatus according to claim 25, wherein a wall of the chamber is provided with a flexibly-movable portion movement of which produces the said volume change.

27. Apparatus according to claim 26, wherein the flexibly-movable portion is movable by means of a drive mechanism.

28. Apparatus according to claim 24, including means for purging the air from the chamber.

29. Apparatus according to claim 24, wherein said chamber is provided with a vent, the dimensions of the chamber and of the vent being such that the air in the chamber and vent resonates at the given repetition rate.

30. Apparatus according to claim 24, wherein the vent has the form of a pipe one end of which opens into the chamber and the other end of which is open to the atmosphere.

31. Apparatus according to claim 24, including X-ray apparatus so arranged in relation to the chamner that the presence of metal objects within a container located in the chamber may be detected thereby.

* * * * *

UNITED STATES PATENT AND TRADEMARK OFFICE
CERTIFICATE OF CORRECTION

PATENT NO. : 3,998,101
DATED : December 21, 1976
INVENTOR(S) : ROBERT F.D. BRADSHAW ET AL It is certified that error appears in the above-identified patent and that said Letters Patent are hereby corrected as shown below:

In the Title page, Section [73], change "U.S. Philips Corporation, New York, N.Y." to --Pye Limited, Cambridge, Mass.--.

Section [30], change "April 30, 1975 37795/75" to --August 29, 1974   3,7795/74--.

Column 1, line 34, change "vaporss" to --vapors--.

Claim 31, line 2, change "chamner" to --chamber--.

Signed and Sealed this

Twenty-sixth Day of April 1977

[SEAL]

Attest:

RUTH C. MASON
Attesting Officer

C. MARSHALL DANN
Commissioner of Patents and Trademarks